United States Patent
Mikhaltsevitch et al.

(10) Patent No.: US 7,282,913 B2
(45) Date of Patent: Oct. 16, 2007

(54) PULSE SEQUENCES FOR EXCITING NUCLEAR QUADRUPOLE RESONANCE

(75) Inventors: Vassili Timofeevitch Mikhaltsevitch, St. James (AU); Taras Nikolaevitch Rudakov, Willetton (AU); John Harold Flexman, Kardinya (AU); Peter Alaric Hayes, Wembly Downs (AU); Warrick Paul Chisholm, Ferndale (AU)

(73) Assignee: Qrsciences Pty. Ltd. (AU)

( * ) Notice: Subject to any disclaimer, the term of this patent is extended or adjusted under 35 U.S.C. 154(b) by 0 days.

(21) Appl. No.: 11/016,728

(22) Filed: Dec. 21, 2004

(65) Prior Publication Data

US 2005/0162163 A1  Jul. 28, 2005

(30) Foreign Application Priority Data

Jun. 21, 2002 (AU) ........................ PS3121
Jun. 20, 2003 (WO) ................. PCT/AU03/00776

(51) Int. Cl.
G01V 3/00 (2006.01)

(52) U.S. Cl. ........................ 324/309; 324/307

(58) Field of Classification Search ............... 324/309
See application file for complete search history.

(56) References Cited

U.S. PATENT DOCUMENTS

| | | | |
|---|---|---|---|
| 5,233,300 A | | 8/1993 | Buess et al. |
| 5,365,171 A | * | 11/1994 | Buess et al. ............... 324/307 |
| 5,608,321 A | | 3/1997 | Garroway et al. |
| 6,127,824 A | * | 10/2000 | Sydney Smith et al. ..... 324/300 |
| 6,208,136 B1 | * | 3/2001 | Smith et al. ................ 324/300 |
| 6,392,408 B1 | * | 5/2002 | Barrall et al. ............... 324/300 |
| 6,577,128 B1 | * | 6/2003 | Smith et al. ................ 324/309 |

FOREIGN PATENT DOCUMENTS

| | | |
|---|---|---|
| GB | 2 200 462 | 8/1988 |
| GB | 2 255 414 | 11/1992 |
| GB | 2 255 414 A | 11/1992 |
| GB | 2 338 787 | 12/1999 |
| SU | 1824559 | 6/1993 |
| SU | 1831680 | 7/1993 |

(Continued)

OTHER PUBLICATIONS

Bushong, S.C., "Magnetic Resonance Imaging Physical and Biological Principles," Mosby-Year Book Inc, St. Louis, Missouri, 1996, pp. 74-80.*

(Continued)

Primary Examiner—Diego Gutierrez
Assistant Examiner—Megann E Vaughn
(74) Attorney, Agent, or Firm—Michael Bednarek; Paul, Hastings, Janofsky & Walker LLP

(57) ABSTRACT

An apparatus and method for producing a multi-pulse sequence for irradiating a substance provided with quadrupole nuclei with either integer or half-integer spins to detect an NQR signal emitted therefrom. The apparatus has pulse sequence generating means adapted to produce multi-pulse sequences with pulse intervals exceeding $T_2^*$ and containing a preparatory pulse or group of pulses for creating echo signals between the pulses. The pulse sequence is organised so that the resulting signal contains a prevailing echo component produced by the preparatory pulse or group of pulses.

12 Claims, 4 Drawing Sheets

FOREIGN PATENT DOCUMENTS

| WO | WO92/17794 | 10/1992 |
| WO | WO 92/17794 | 10/1992 |
| WO | WO 93/11441 | 6/1993 |
| WO | WO93/11441 | 6/1993 |
| WO | WO96/26453 | 8/1996 |
| WO | WO 96/26453 | 8/1996 |
| WO | WO 99/19740 | 4/1999 |
| WO | WO99/19740 | 4/1999 |

OTHER PUBLICATIONS

Puddephat, M.P., "Principles of Magnetic Resonance Imaging," posted Dec. 21, 2002.*

Flexman et al., "The Detection of Explosives in Airport Luggage Using the Direct Nuclear Quadrupole Resonance Method," Detection of Bulk Explosives Advanced Techniques Against Terrorism, Proceedings of the NATO Advanced Research Workshop, held in St. Petersburg, Russia, Jun. 16-21, 2003, Series: NATO Science Series II: Mathematics, Physics and Chemistry, Schubert, Hiltmar; Kuznetsov, Andrey (eds.), vol. 138, 2004, pp. 113-124.

Garroway et al., "Explosives Detection by Nuclear Quadrupole Resonance (NQR)," SPIE, vol. 2276, 1994, pp. 139-149.

Garroway et al., "Narcotics and Explosives Detection by $^{14}$N Pure NQR," SPIE, vol. 2092, 1993, pp. 318-327.

Chen and Slichter, "Zero-Field NMR Study on a Spin-Glass: Iron-Doped 2H-Niobium Diselenide," Physical Review B, vol. 27, No. 1, Jan. 1, 1983, pp. 278-292.

Vega et al., "Cu Nuclear Quadrupole Resonance of $YBa_2Cu_3O_x$ With Varying Oxygen Content," Physical Review B, vol. 39, No. 4, 1989, pp. 2322-2332.

Kreis et al, "Low Frequency Pulse Excitation in Zero Field Magnetic Resonance," Journal of Chemical Physics, vol. 89, No. 11, 1988, pp. 6623-6635.

Erickson, Optically Detected Multipulse Nuclear-Quadrupole-Resonance Studies of Trivalent Praseodymium in Zero and Weak Static Magnetic Fields, Physical Review B, vol. 39, No. 10, Apr. 1989, pp. 6342-6347.

Singh and Armstrong, "Spin Thermodynamics Applied to Pure Nuclear Quadrupole Resonance for an Inhomogeneously Broadband Line in a Spin-3/2 System," Journal of Physics C: Solid State Physics, vol. 19, 1986, pp. L221-L227.

Bai et al., "Zeeman-Perturbed Spin-Echo FT NQR Spectroscopy," Journal of Magnetic Resonance Series A, vol. 102, 1993, pp. 137-143.

Shastri et al., "Distribution of Non-equivalent Aluminium Sites Revealed in Al-Cu-Ru and Al-Cu-Fe Quasicrystals by $^{27}$Al NQR," Physical Review B, vol. 50, No. 6, Aug. 1, 1994, pp. 4224-4227.

Nickel and Kimmich, "2D Exchange NQR Spectroscopy," Journal of Molecular Structure, vol. 345, 1995, pp. 253-264.

Kohori et al., "$^{27}$Al NMR and NQR Studies of the Antiferromagnetic Superconductor $UPd_2Al_3$," Solid State Communications, vol. 95, No. 2, 1995, pp. 121-126.

Peterson and Oja, "A Pusled Nuclear Quadrupole Resonance Spectrometer," Advances in Nuclear Quadrupole Resonance, vol. 1, ed. J. A. S. Smith (London: Heyden), 1974, pp. 179-184.

Ramachandran and Narasimhan, "A Coherent Nuclear Quadrupole Pulse and Double Resonance Spectrometer," Journal of Physics E: Scientific Instruments, vol. 16, 1983, pp. 643-648.

Harding et al., "A Pulsed NQR-FFT Spectrometer for Nitrogen-14," Journal fo Magnetic Resonance, vol. 36, 1979, pp. 21-33.

Hirshfeld and Klainer, "Short Range Remote NQR Measurements," Journal of Molecular Structure, vol. 58, 1980, pp. 63-77.

Grechiskin, "NQR Device for Detecting Plastic Explosives, Mines and Drugs," Applied Physics A, vol. 55, 1992, pp. 505-507.

Grechishkin and Sinyavskii, "Remote Nuclear Quadrupole Resonance in Solids," Physics—Uspekhi, vol. 38, No. 10, 1993, pp. 980-1003.

Grechishkin, "Application of Multipulse Sequences in Remote NQR," Applied Physics A, vol. 58, 1994, pp. 63-65.

Klainer et al., "Fourier Transform Nuclear Resonance Spectroscopy," in "Fourier, Hadamard and Hilbert Transforms in Chemistry," A. G. Marshall, ed., Plenum, New York, 1982, pp. 147-182.

Hitrin et al., "Pulsed Spin Locking Theory in Pure Quadrupole Resonance," Journal of Molecular Structure, vol. 83, No. 1-2, 1982, pp. 269-275.

Maricq, "Quasistationary State and Its Decay to Equilibrium in the Pulsed Spin Locking of a Nuclear Quadrupole Resonance," Physical Review B, vol. 33, No. 7, Apr. 1, 1986, pp. 4501-4513.

Marino and Klainer, "Multiple Spin Echoes in Pure Quadrupole Resonance," Journal of Chemical Physics, vol. 67, No. 7, 1977, pp. 3388-3389.

Osokin et al., "The Quasistationary States in Multipulse NQR," Z. Naturforsch, vol. 47a, 1992, pp. 439-445.

Bradford et al., "A Steady-State Transient Technique in Nuclear Induction," Physical Review, vol. 84, No. 1, 1951, pp. 157-158.

Carr, "Steady-State Free Precession in Nuclear Magnetic Resonance," Physical Review, vol. 112, No. 5, 1958, pp. 1693-1701.

Erofeev et al., "Relaxation of Nuclear Magnetization Under Many-Pulse NMR Experimental Conditions," Sov. Phys. JETP, vol. 48, No. 5, 1978, pp. 925-930.

Ivanov et al., "Thermodynamics Theory of Narrowing of NMR Spectral Lines in Solids," Sov. Phys. JETP, vol. 48, No. 5, 1978, pp. 930-936.

Ernst and Anderson, "Application of Fourier Transform Spectroscopy to Magnetic Resonance," Rev. Sci. Instr., vol. 37, No. 1, 1966, pp. 93-102.

Decorps et al., "An Inductively Coupled, Series-Tuned NMR Probe," Journal of Magnetic Resonance, vol. 65, 1985, pp. 100-109.

Suits et al., "Super-Q Detection of Transient Magnetic Resonance Signals," Journal of Magnetic Resonance, vol. 132, 1998, pp. 54-64.

Rudakov et al., "Damping of Transients in an Excited Circuit of an NQR Spectrometer," Instruments and Experimental Techniques, vol. 38, No. 6, Part 1, 1995, pp. 744-745.

Hoult, "Fast Recovery, High Sensitivity NMR Probe and Preamplifier for Low Frequencies," The Review of Scientific Instruments, vol. 50, No. (2), Feb. 1979, pp. 193-200.

Conradi, "FET Q Switch of rPulsed NMR," The Review of Scientific Instruments, vol. 48, No. 3, Mar. 1977, pp. 359-361.

Samuelson et al.; "Self-Switching Damping Circuit for Reducing Transmitter Ringdown Time in High Power Pulse NMR," The Review of Scientific Instruments, vol. 41, No. 11, Nov. 1970, pp. 1601-1603.

* cited by examiner

US 7,282,913 B2

PULSE SEQUENCES FOR EXCITING NUCLEAR QUADRUPOLE RESONANCE

BACKGROUND OF THE INVENTION

This application claims priority to Australian Provisional Patent Application No. PS 3121 filed on Jun. 21, 2002 and to International Application No. PCT/AU03/00776 filed on Jun. 20, 2003.

FIELD OF THE INVENTION

The present invention relates to the practical use of the nuclear quadrupole resonance (NQR) phenomenon for identifying substances that contain quadrupole nuclei, particularly for identifying explosive or narcotic substances.

The invention has particular utility in multi-pulse radio frequency (RF) excitation of quadrupole nuclei and to the subsequent measurement of the NQR signal emitted therefrom where changes in temperature can effect measurement.

Throughout the specification, unless the context requires otherwise, the word "comprise" or variations such as "comprises" or "comprising", will be understood to imply the inclusion of a stated integer or group of integers but not the exclusion of any other integer or group of integers.

The term "preparatory pulse" means both a separate preparatory pulse and a group of preparatory pulses.

Furthermore, "a group of preparatory pulses" means a group of pulses that precede a multi-pulse sequence distributed within a time interval $<3T_2$ ($T_2$ being the time of dipole-dipole relaxation), during which the NQR signal, as a rule, is not measured.

BACKGROUND ART

The following discussion of the background art is intended to facilitate an understanding of the present invention only. It should be appreciated that the discussion is not an acknowledgement or admission that any of the material referred to is or was part of the common general knowledge as at the priority date of the application.

To detect explosive and narcotic substances by means of multi-pulse NQR, steady state free precession (SSFP) type pulse sequences are usually preferred. The principal reasons for this preference are as follows:

1. It is possible to receive a continuous chain of signals if the requirement $$n \cdot \omega_{\mathit{eff}} \neq m \cdot \frac{\pi}{\tau} \quad (1)$$

is met. Here, $\tau$ is the pulse spacing of the sequence, n and m are whole numbers, $\omega_{\mathit{eff}}$ represents the effective field which substitutes the effect of the RF pulses and the resonance offset, ensuring unlimited time for signal accumulation.
2. It is possible to receive an NQR signal phase that is different from the phase of the irradiating pulses, which can be used for cancelling intensity anomalies, or for subtracting spurious signals.
3. Comparatively little RF power is required for detecting samples in large volumes When requirement (1) is met, the SSFP sequences allow achievement of a greater signal-to-noise ratio per unit of time than any other multi-pulse sequences used for exciting the quadrupole spin system.

However, complying with condition (1) cannot be guaranteed in practice because the exact value of the resonance offset in most cases is unknown due to the fact that the exact temperature of the sample is not known either.

The dependence of the signal intensity on the resonance offset when using the SSFP sequences is characterised by the existence of intensity anomalies.

In the solid state when irradiating sequence parameters approach the resonance conditions, intensity anomalies are manifested specifically by the the amplitude reducing and damping of the signal accelerating as indicated by the equation:

$$n \cdot \omega_{\mathit{eff}} = m \cdot \frac{\pi}{\tau}, \quad (2)$$

which can result in a sharp decline in the signal intensity or even in the complete loss of information about the presence (or absence) of the sample in the examined volume.

The temperature dependence of the resonance frequencies of quadrupole nuclei in a number of substances is quite considerable. For example, for RDX at frequency $v_+ = 5.192$ MHz and at temperatures close to room temperature, the change in $^{14}N$ resonance frequency is $-520$ Hz/° K. For PETN at $^{14}N$ frequency $v_+ = 890$ kHz, it is $-160$ Hz/° K; and for $KNO_3$ at nitrogen line $v_+ = 567$ kHz, it is $-140$ Hz/° K.

The $^{14}N$ NQR intensity anomalies were first demonstrated using a basic SSFP sequence of identical coherent RF pulses.

For the purpose of detecting explosive and narcotic substances, the SSFP type pulse sequences are followed by echo sequences. Multi-pulse versions of echo sequences refer to the class of saturating sequences, which exist because of the condition of the inequality $T_2^* < \tau << T_1$.

Saturating properties of this type of sequence cause total decay of the NQR signals at any frequency offset and flip angle. The time of the signal decay is determined by the time constant $T_{1e}$ ("effective relaxation time") and has a value within the limits $T_2 \leq T_{1e} < T_1$ (or, to be more exact, $T_2 \leq T_{1e} < T_{1\rho}$, where $T_{1\rho}$ is the relaxation time in a rotating frame of axis and where $T_{1\rho}$ should always be less than $T_1$ ($T_{1\rho} < T_1$)).

In a number of cases, using echo sequences is preferable to using the SSFP-type sequences. This is true when working with high Q detectors, where the "dead time" of the receive system of the spectrometer is comparable in value with $T_2^*$ time, and there exists the possibility to generate echo-signals which exceed the "dead time". Hence echo sequences considerably increase the detection capability while reducing the requirements on the Q-switch system.

However, up to this point, intensity anomalies of echo signals after irradiation with multi-pulse sequences for the purpose of obtaining NQR have not been studied.

DISCLOSURE OF THE INVENTION

The principal object of the present invention is to increase the accuracy of detection of certain prescribed substances in specimens, compared with the previously known methods of detecting same using NQR, by reducing temperature effects. Such prescribed substances may include, but are not limited to, certain explosives and narcotics.

As temperature effects are based on the intensity anomalies effect, a preferred object of the invention is to increase the accuracy of detecting certain prescribed substances such as explosives and narcotics by reducing the intensity anomalies effect.

The purpose of the invention is generally achieved by using multi-pulse sequences with pulse intervals exceeding $T_2^*$ and containing a preparatory pulse or group of preparatory pulses for creating echo signals between the pulses, organised so that the resulting signal contains a prevailing echo component produced by the preparatory pulse or group of preparatory pulses.

The invention arises from the discovery, both theoretically and experimentally, that echo-sequences under certain conditions practically do not create intensity anomalies, and this permits detecting substances of interest in less time and with greater reliability.

In practical terms, the invention has great utility in the detection of substances containing nitrogen nuclei $^{14}N$ with long spin-lattice relaxation times $T_1$, although the invention is not limited to this area.

In accordance with a first aspect of the present invention, there is provided a nuclear quadrupole resonance apparatus for detecting a target substance containing quadrupole nuclei, comprising:

a pulse sequence generator to generate a combination of multi-pulse sequences with pulse intervals longer than the time constant of free induction decay $T_2^*$, but shorter than the time of spin-spin relaxation $T_2^*$, and to generate a preparatory pulse or group of preparatory pulses for creating echo signals between the pulses of the multi-pulse sequences;

a detector to detect nuclear quadrupole resonance signals generated from the target substance under conditions of unknown temperature of the target substance in response to the combination of multi-pulse sequences; and a combiner to combine the detected nuclear quadrupole resonance signals generated under conditions of unknown temperature of the target substance into a resulting signal such that the resulting signal contains a prevailing echo component produced by the preparatory pulse or group of preparatory pulses, thereby mitigating the effect of intensity variations.

In accordance with a second aspect of the present invention, there is provided a method of nuclear quadrupole resonance for detecting a target substance containing quadrupolar nuclei, the method comprising the steps of:

generating a combination of multi-pulse sequences, at least one of which contains a preparatory pulse or group of preparatory pulses, having intervals between pulses longer than the time constant of free induction decay $T_2^*$, but shorter than the time of spin-spin relaxation $T_2^*$;

irradiating the target substance with the combination of multi-pulse sequences;

detecting nuclear quadrupole resonance signals generated from the target substance under conditions of unknown temperature of the target substance in response to the combination of multi-pulse sequences; and combining the detected nuclear quadrupole resonance signals generated under conditions of unknown temperature of the target substance into a resulting signal where echo generated by the preparatory pulse or group of preparatory pulses is a prevailing component, thereby mitigating the effect of intensity variations.

Preferably, the combination contains at least one sequence.

Preferably, the flip angles of pulses of sequences of the combination range between 60° and 345°

Preferably, at least one preparatory pulse is composite.

Preferably, all pulse sequences of the combination contain a preparatory pulse or a group of preparatory pulses.

Preferably, the carrier frequency of the pulse sequences is near to one of NQR frequencies of the target substance to be detected.

Preferably, the target substance to be detected comprises an explosive containing quadrupole nuclei.

Alternatively, it is preferred that the target substance to be detected comprises a narcotic containing quadrupole nuclei.

In accordance with a third aspect of the present invention, there is provided an apparatus for producing a multi-pulse sequence for irradiating a target substance containing quadrupole nuclei, comprising:

a generator to generate a combination of multi-pulse sequences with pulse intervals longer than the time constant of free induction decay $T_2^*$, but shorter than the time of spin-spin relaxation $T_2^*$, and containing a preparatory pulse or group of preparatory pulses for creating echo signals between the pulses of the multi-pulse sequences organised so that the resulting signal contains a prevailing echo component produced by the preparatory pulse or group of preparatory pulses; and a detector to detect nuclear quadrupole resonance signals generated from the target substance under conditions of unknown temperature of the target substance in response to the combination of multi-pulse sequences.

In accordance with a fourth aspect of the present invention, there is provided a nuclear quadrupole resonance apparatus for detecting a target substance containing quadrupole nuclei, the apparatus comprising:

means for generating a combination of multi-pulse sequences with pulse intervals longer than the time constant of free induction decay $T_2^*$, but shorter than the time of spin-spin relaxation $T_2^*$, and for generating a preparatory pulse or group of preparatory pulses for creating echo signals between the pulses of the multi-pulse sequences;

means for detecting nuclear quadrupole resonance signals generated from the target substance under conditions of unknown temperature of the target substance in response to the combination of multi-pulse sequences; and means for combining the detected nuclear quadrupole resonance signals into a resulting signal such that the resulting signal contains a prevailing echo component produced by the preparatory pulse or group of preparatory pulses, thereby mitigating the effect of intensity variations.

In accordance with a fifth aspect of the present invention, there is provided an apparatus for producing a multi-pulse sequence for irradiating a target substance provided with quadrupole nuclei, comprising:

generator means for generating a combination of multi-pulse sequences with pulse intervals longer than the time constant of free induction decay $T_2^*$, but shorter than the time of spin-spin relaxation $T_2$ and containing a preparatory pulse or group of preparatory pulses for creating echo signals between the pulses of the multi-pulse sequences organised so that the resulting signal contains a prevailing echo component produced by the preparatory pulse or group of preparatory pulses; and detector means for detecting nuclear quadrupole resonance signals generated from the target substance under conditions of unknown temperature of the target substance in response to the combination of multi-pulse sequences.

In accordance with a sixth aspect of the present invention, there is provided a pulse sequence signal for irradiating a target substance provided with quadrupole nuclei, the pulse sequence signal comprising:

a combination of multi-pulse sequences with pulse intervals longer than the time constant of free induction decay $T_2^*$, but shorter than the time of spin-spin relaxation $T_2$; and a preparatory pulse or group of preparatory pulses for creating echo signals between the pulses of the multi-pulse sequences, the pulse sequence signal being arranged for irradiating a target substance under conditions of unknown temperature of the target substance, and operable to mitigate the effect of intensity variations.

In accordance with a seventh aspect of the present invention, there is provided a pulse sequence for irradiating a target substance provided with quadrupole nuclei, the pulse sequence comprising:

a combination of multi-pulse sequences with pulse intervals longer than the time constant of free induction decay $T_2^*$, but shorter than the time of spin-spin relaxation $T_2$; and a preparatory pulse or group of preparatory pulses for creating echo signals between the pulses of the multi-pulse sequences, the pulse sequence being arranged for irradiating a target substance under conditions of unknown temperature of the target substance, and operable to mitigate the effect of intensity variations.

BRIEF DESCRIPTION OF THE DRAWINGS

The invention will be better understood in relation to the following description of several embodiments thereof. The description is made with reference to the following drawings, wherein:

FIGS. 3a and 3b show the experimental dependence of the amplitudes of the NQR Fourier transform of the difference between the carrier frequency of the RF pulses of the SLSE sequence and the frequency of the resonance transition received at room temperature and the same parameters of the SLSE as the theoretical curves in FIGS. 2a and 2b respectively, wherein FIG. 3a depicts a received signal from an HMX sample and FIG. 3b depicts a received signal from $NaNO_2$ powder;

BEST MODE(S) FOR CARRYING OUT THE INVENTION

Figure 1:
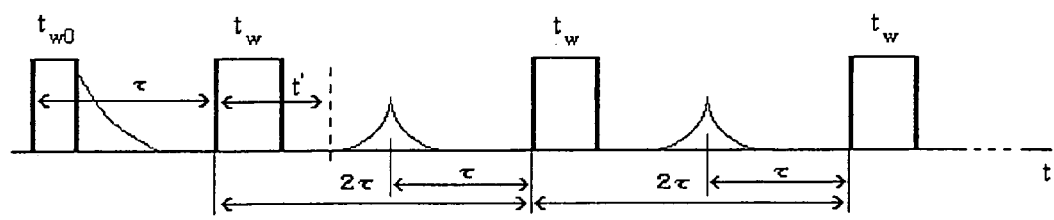
FIG. 1 is a timing diagram showing the spin locking of the spin echo pulse sequence (SLSE) with all of the relevant parameters designated.

In order to justify the use of echo signals in multi-pulse sequences for eliminating intensity anomalies and thus provide for the best mode for carrying out the invention, a simplified theoretical analysis will be undertaken of the dependence of the echo signal on the frequency offset in the spin locking spin echo (SLSE) sequence represented by:

$$\phi_{0x}-(\tau-\phi_y-\tau)_n,$$

where the bottom index at the flip angle sign $\phi$ designates the phase of the carrier frequency for the RF pulse, n is the number of cycles of the sequence, and $\tau$ is the time interval between the preparatory pulse and the first pulse of the sequence. The results of this analysis will then be compared with experimental data to verify the correlation.

Thus the analysis is carried out in accordance with the following procedure.

Firstly, the echo signal in the sequence $(\phi_0)_{0°}-(\tau-\phi_{90°}-\tau)_n$ is determined for the times $t \leq T_2$. The "spin locking" effect of the echo signal is then considered in terms of the concept of the effective field of a multi-pulse sequence. The essence of the effective field concept is to replace the effects of the real RF pulses and the resonance offset by a certain fictitious uninterrupted field. Using this concept, the echo signal in the interval between the n and n+1 pulses is determined, after which the Fourier transform of the signal is found and powder averaging is performed.

After that the echo signal is determined for the times $t > T_2$ and N signal averages are carried out (N being the number of pulses in a pulse sequence) taking into account the spin-lattice relaxation. The dependence of the resulting signal against the resonance offset is plotted and the obtained dependence is compared with experimental results.

Now having regard to a crystalline sample containing spin-1 nuclei. It is assumed that the quadrupole principal axes for each of the spins have the same orientation. The quadrupole Hamiltonian in the quadrupole principal axes frame is given as:

$$H_q = \frac{e^2qQ}{4I(2I-1)}[3I_z^2 - I^2 + \eta(I_x^2 - I_y^2)], \qquad (1)$$

where $e^2qQ$ is the nuclear quadrupole coupling constant, and $\eta$ is the asymmetry parameter of the electric field gradient tensor.

In terms of the fictitious spin-½ operators $H_q$ takes the form:

$$H_q = \frac{e^2qQ}{4}(I_{x,3} - I_{y,3} - I_{z,3}) = \omega_p I_{p,3} + \omega'_p I_{p,4} \qquad (2)$$

with $$\omega_x = \frac{e^2qQ}{4}(\eta+3), \omega_y = \frac{e^2qQ}{4}(\eta-3), \omega_z = -\frac{e^2qQ}{2}\eta; \qquad (3)$$

-continued $$\omega'_x = \frac{e^2qQ}{4}(\eta - 1), \omega'_y = \frac{e^2qQ}{4}(\eta + 1), \omega'_z = -\frac{e^2qQ}{2}\eta, \quad (4)$$

or $$\omega'_p = \frac{1}{3}(\omega_q - \omega_r). \quad (5)$$

Here the Hamiltonian $H_q$ is written in frequency units (h=1), p,q,r=x,y,z or cyclic permutation.

The three parameters $\omega_x$, $\omega_y$ and $\omega_z$, which have the dimension of angular frequency, are linked with the three transition frequencies $\omega_+$, $\omega_-$ and $\omega_0$ between the quadrupolar energy level equalities $\omega_x = \omega_+$, $\omega_y = -\omega_-$, $\omega_z = -\omega_0$. The parameters $\omega_x$, $\omega_y$, $\omega_z$ are treated as being equivalent to the resonant frequencies $\omega_+$, $\omega_-$, $\omega_0$, which will be described in more detail later, where one of these three transitions is considered with an arbitrary frequency $\omega_p$.

In this simplified one-particle analysis, all kinds of multi-particle interactions are neglected, as is the spin-lattice relaxation.

The interaction of quadrupolar nuclei with the radio frequency field is described with an RF Hamiltonian as follows:

$$H_1(t) = -2\gamma \cdot H_1(\sin\vartheta_X I_{x,1} + \sin\vartheta_Y I_{y,1} + \\ + \cos\vartheta_Z I_{z,1})\cos(\omega t + \phi) = \cos(\omega t + \phi)\sum_{m=x,y,z} a_m I_{m,1} \quad (6)$$

where $a_x = \gamma H_1 \cdot \sin\Theta_L \cdot \cos\phi_L$, $a_y = \gamma H_1 \cdot \sin\Theta_L \cdot \sin\phi_L$, $\gamma$ is the gyromagnetic ratio, $H_1$ is the amplitude of the RF field, $\phi$ is its initial phase, $\Theta_L$ and $\phi_L$ are the polar and azimuthal angles of the field vector in the principal axes frame, and $\omega$—is the carrier frequency of the RF pulses.

Now considering a transformation into the interaction representation defined by the Hamiltonian:

$$H_0 = \omega \cdot I_p + W_p I_{p,4} = \quad (7)$$

$$= \omega_q I_{q,3} + W_q I_{q,4} = \quad (8)$$

$$= \omega_r I_{r,3} + W_r I_{r,4}. \quad (9)$$

Here $$W_p=(\omega_q-\omega_r)/3; \; W_q=(\omega_r-\omega)/3; \; W_q=(\omega-\omega_q)/3. \quad (10)$$

The secular independent of the time part of the RF Hamiltonian in the $H_0$ representation looks as follows:

$$\tilde{H}_1 = \exp(-iH_0 t)H_1(t)\exp(iH_0 t) = -\omega_1[\cos\phi \cdot I_{p,1} + \sin\phi \cdot I_{p,2}], \quad (11)$$

where ($\omega_1 = a_p$).

In the $H_0$ representation the evolution of the density matrix $\tilde{\rho}$ ($\tilde{\rho}(t) = \exp(-iH_0 t)\rho(t)\exp(iH_0 t)$) during the impact of the RF pulses is described by the equation $$i\frac{d\tilde{\rho}}{dt} = [\tilde{H}_1, \tilde{\rho}] \quad (12)$$

and in the intervals between the pulses it is described by $$i\frac{d\tilde{\rho}}{dt} = [\Delta\omega I_{p,3}, \tilde{\rho}]. \quad (13)$$

Here and later on, all calculations and results will be done in $H_0$ representation, so the tilde notation will be dropped.

Parameters of the SLSE are shown in FIG. 1.

It should be noted that in this case, $t_\omega \ll \tau$.

The interaction with the k-pulse of the pulsed sequence is:

$$H_{rf} = -f(t)(I_{p,1}\cos\phi_k + I_{p,2}\sin\phi_k) \quad (14)$$

where $\phi_k$ is the phase of the k-pulse of the sequence; and f(t) is the pulsed function:

$$f(t) = \omega_1 \sum_{k=0}^{\omega} \delta(\tau + 2k\tau - t). \quad (15)$$

The equation (12) may be rewritten in the form:

$$i\frac{d\rho}{dt} = [\omega_e I_p, \rho] \quad (16)$$

Here $\omega = \omega_e e$, $e = (e_x, e_y, e_z)$ is the unit vector:

$$e_x = -\frac{\omega_1 \cdot \cos\phi_k}{\omega_e}, \; e_y = -\frac{\omega_1 \cdot \sin\phi_k}{\omega_e}, \; e_z = \frac{\Delta\omega}{\omega_e}, \; \omega_e = (\omega_1^2 + \Delta\omega^2)^{\frac{1}{2}};$$

and $I_p$ is the vector in $I_{p,i}$-operator space.

Before the impact of the RF pulses, the spin system is in equilibrium and the density matrix is described by the expression:

$$\rho_0 = \frac{N}{2I+1}\exp\left(-\frac{H_q}{kT}\right),$$

where N is the number of units in the system; k is the Boltzmann's constant; and I is the spin of the nuclei.

In the high-temperature approximation for nitrogen-14, I=1, and consequently:

$$\rho_0 = \frac{N}{3}\left(E - \frac{H_q}{kT}\right) = \frac{N}{3}(E - \alpha_0 H_q) \quad (17)$$

where $$\alpha_0 = \frac{1}{kT}$$

is a reverse spin temperature.

The solution for equation (16) during the impact of the preparatory pulse $t_{w0}$ ($\phi=0$) looks as follows:

$$\rho(t_{w0}) = \frac{N}{3}[E - \alpha_0 \omega_p n_0 I_p - \alpha_0 W_p I_{p,4}],$$

where $n_0 = (n_{01}, n_{02}, n_{03})$ is a unit vector with components:

$$n_{01} = -\frac{\Delta\omega \cdot \omega_1}{\omega_e^2}(1 - \cos\varphi_0), \quad n_{02} = \frac{\omega_1}{\omega_e}\sin\varphi_0, \quad n_{03} = \frac{\Delta\omega^2 + \omega_1^2\cos\varphi_0}{\omega_e^2},$$

where $\phi_0 = \omega_e t_{w0}$.

In the case when $\omega_1 \gg \Delta\omega$ it can be assumed that:

$$n_{01} \approx 0, \quad n_{02} \approx \sin\phi_0, \quad n_{03} \approx \cos\phi_0. \tag{18}$$

All the sequence pulses that follow the preparatory pulse have equal duration $t_w \ll \tau$ and carrier frequency phases $$\phi_k = \frac{\pi}{2}.$$

An effective field $\omega_{\text{eff}}$ will now be introduced, which substitutes the effect of the RF pulses and the resonance offset, by dependences:

$$\exp(-i\omega_{\text{eff}} I_p 2\tau) = \exp(-i\omega_{\text{eff}} k \cdot I_p 2\tau) \tag{19}$$
$$= \exp(-i\Delta\omega\tau I_{p,3})\exp(-i\omega_e I_p t_w)$$
$$\exp(-i\Delta\omega\tau I_{p,3})$$
$$= \left(\cos\frac{\Delta\omega \cdot \tau}{2} - i2I_{p,3}\sin\frac{\Delta\omega \cdot \tau}{2}\right)$$
$$\left(\cos\frac{\varphi}{2} - i2eI_p\sin\frac{\varphi}{2}\right) \times$$
$$\left(\cos\frac{\Delta\omega \cdot \tau}{2} - i2I_{p,3}\sin\frac{\Delta\omega \cdot \tau}{2}\right)$$

Here $\phi = \omega_e t_w$; at $\omega_1 \gg \Delta\omega$, so it can be accepted that $\phi \approx \omega_1 t_w$.

A unit vector is then defined as follows:

$$k = (k_1, k_2, k_3), \quad k = \frac{\omega_{\text{eff}}}{|\omega_{\text{eff}}|}, \quad |\omega_{\text{eff}}| = \omega_{\text{eff}}.$$

Assuming $\omega_1 \gg \Delta\omega$, then from (19):

$$\cos(\omega_{\text{eff}}\tau) = \cos\frac{\varphi}{2} \cdot \cos\Delta\omega\tau; \quad k_1 = 0; \quad k_2 = -\frac{\sin\frac{\varphi}{2}}{\sin\omega_{\text{eff}}\tau}; \tag{20}$$

$$k_3 = \frac{1}{\sin\omega_{\text{eff}}\tau}\cos\frac{\varphi}{2}\sin\Delta\omega\tau.$$

Here for the sake of convenience, an effective time-independent Hamiltonian is defined as:

$$H_{\text{eff}} = \omega_{\text{eff}} I_p. \tag{21}$$

From the moment t=0, when the induction signal reaches its maximum, the evolution of the spin system starts to be determined by the Hamiltonian (21) as:

$$\rho(2n\tau) = \exp(-iH_{\text{eff}} \cdot 2n\tau) \cdot \rho(2\tau) \cdot \exp(iH_{\text{eff}} \cdot 2n\tau) \tag{22}$$

The evolution of the system set by expression (22), is equivalent to the rotation of the operator of the angular momentum described by expression:

$$I'_p = \exp(-i\theta k I_p) I_p \exp(+i\theta k I_p) \tag{23}$$
$$= k(k \cdot I_p) + (I_p - k(k \cdot I_p))\cos\theta - (k \times I_p)\sin\theta.$$

Thus, assuming $\theta = 2n\tau\omega_{\text{eff}}$ and bearing in mind equations (17) and (23), the following arises:

$$\rho(2n\tau) = -\frac{\alpha_0 \omega_p N}{3} n_0 I'_p \tag{24}$$
$$= -\frac{\alpha_0 \omega_p N}{3}[I_{p,1}\{-n_{02}k_3\sin(\omega_{\text{eff}}2n\tau) +$$
$$n_{03}k_2\sin(\omega_{\text{eff}}2n\tau)\} + I_{p,2}\{n_{02}k_2^2 + n_{02}(1 -$$
$$k_2^2)\cos(\omega_{\text{eff}}2n\tau) + n_{03}k_2k_3(1 - \cos(\omega_{\text{eff}}2n\tau))\} +$$
$$I_{p,3}\{n_{02}k_2k_3(1 - \cos(\omega_{\text{eff}}2n\tau)) + n_{03}k_3^2 +$$
$$n_{03}(1 - k_3^2)\cos(\omega_{\text{eff}}2n\tau)\}].$$

The echo is always proportional to $n_{02}$, but not all parts of the density matrix which are proportional to $n_{02}$ describe the echo. To separate the echo from the received expression, it is necessary to determine the density matrix $\rho'(2n\tau)$ for sequence $(\phi_0)_{0°} - (\tau - \phi_{0°} - \tau)_n$, which contains identical expressions for all components of the density matrix proportional to $n_{02}$, with the exception of the fact that the echo components of the operator $\rho'(2n\tau)$ have the opposite sign.

Repeating the above procedure results in:

$$\rho'(2n\tau) = -\frac{\alpha_0 \omega_p N}{3}[I_{p,1}\{-k_{2\text{echo}}k_3\sin(2n\tau\omega_{\text{eff}}) + \tag{25}$$
$$k_{3\text{echo}}k_2k_3(1 - \cos(2n\tau\omega_{\text{eff}}))\} +$$
$$I_{p,2}(k_{2\text{echo}}\cos(2n\tau\omega_{\text{eff}}) - k_{3\text{echo}}k_2\sin(2n\tau\omega_{\text{eff}}))\} +$$
$$I_{p,3}\{k_{2\text{echo}}k_2\sin(2n\tau\omega_{\text{eff}}) + k_{3\text{echo}}k_3^2 +$$
$$k_{3\text{echo}}(1 - k_3^2)\cos(2n\tau\omega_{\text{eff}})\}].$$

Then, leaving in expressions (24) and (25) only parts proportional to $n_{02}$, and subtracting them one from the other, the echo part of the density matrix is derived as:

$$\rho_{\text{echo}}(2n\tau) = -\frac{\alpha_0 \omega_p N}{3} \cdot 2n_{02}k_2^2 I_{p,2}\sin^2(\omega_{\text{eff}}n\tau). \tag{26}$$

Both the in-phase and quadrature components of the echo after the n-th pulse of the sequence are:

$$M_1(2n\tau) = 2Tr(\rho_{\text{echo}}(2n\tau)I_{p,1}) = 0, \tag{27}$$
$$M_2(2n\tau) = 2Tr(\rho_{\text{echo}}(2n\tau)I_{p,2})$$

$$= -\frac{\alpha_0 \omega_p N}{3} \cdot \frac{2\sin^2(\omega_{eff} n\tau) \cdot \sin^2\frac{\varphi}{2}}{\sin^2(\omega_{eff}\tau)} \cdot \sin\varphi_0.$$

The density matrix at arbitrary point t, within the pulse interval (FIG. 1) equals:

$$\rho_{echo}([2n\tau-\tau]+t')=exp(iH_{eff}(t'-\tau))\rho_{echo}(2n\tau)exp(-iH_{eff}(t'-\tau)). \quad (28)$$

From (28) finally received is:

$$M_1([2n\tau - \tau] + t') = 2Tr(\rho_{echo}([2n\tau - \tau] + t')I_{p,1}) \quad (29)$$

$$= -\frac{\alpha_0 \omega_p N}{3} \cdot n_{02}k_2^2 \cdot \sin^2(\omega_{eff} n\tau) \cdot \sin(\Delta\omega(t' - \tau)),$$

$$M_2([2n\tau - \tau] + t') = 2Tr(\rho_{echo}([2n\tau - \tau] + t')I_{p,2})$$

$$= -\frac{\alpha_0 \omega_p N}{3} \cdot n_{02}k_2^2 \cdot \sin^2(\omega_{eff} n\tau) \cdot \cos(\Delta\omega(t' - \tau)).$$

The expression (35) is only true for times <$T_2$.

After a time of ~3$T_2$ the density matrix $\rho_{st}$ is determined totally by the effective Hamiltonian (21). Non-commuting with $H_{eff}$ parts of the density matrix (27) decay and the density matrix $\rho_{st}$ equals:

$$\rho_{st} = H_{eff} \frac{Tr\{H_{eff}\rho(t_{w0})\}}{Tr\{H_{eff}\}^2} = -\frac{\alpha_0 \omega_p N}{3} \cdot (n_{02}k_2 + n_{03}k_3) \cdot (k \cdot I_p).$$

The echo creating part of the density matrix $\rho_{echo-st}$ is proportional to $n_{02}$:

$$\rho_{echo-st} = -\frac{\alpha_0 \omega_p N}{3} \cdot n_{02}k_2 \cdot (k \cdot I_p). \quad (30)$$

For the arbitrary point t':

$$\rho_{echo-st}(t')=exp(iH_{eff}(t'-\tau))\rho_{echo-st}exp(-iH_{eff}(t'-\tau)).$$

Consequently:

$$M_{1-st} = 2Tr(\rho_{echo-st}I_{p,1}) = -\frac{\alpha_0 \omega_p N}{3} \cdot n_{02}k_2^2 \cdot \sin(\Delta\omega(t' - \tau)), \quad (31)$$

$$M_{2-st} = 2Tr(r_{echo-st}I_{p,2}) = -\frac{\alpha_0 \omega_p N}{3} \cdot n_{02}k_2^2 \cdot \cos(\Delta\omega(t' - \tau)).$$

Thus, the maximum amplitude that the echo signal will reach in the sequence window which is removed from the preparatory pulse by the time>$T_2$, equals:

$$M_{st} = |M_{2-st}| = \frac{\alpha_0 \omega_p N}{3} \cdot \frac{\sin^2\frac{\varphi}{2} \cdot |\sin\varphi_0|}{1 - \cos^2\frac{\varphi}{2}\cos^2\Delta\omega\tau}. \quad (32)$$

It should be noted that the solution (32) is arrived at with neglecting the influence of the effective relaxation time $T_{2e}$ and the echo signal shape.

Keeping in mind that for most explosive and narcotic substances the NQR signal line has the Lorentz line shape, the real echo-signal after the n-th pulse can be presented as follows:

$$M_{echo}(t) = M_{echo}([2n - 1]\tau + t') \quad (33)$$

$$= M_{st}(t')\exp\left(-\frac{[2n - 1]\tau + t'}{T_{2e}}\right) \cdot \exp\left(-\frac{1}{T_2^*} \cdot |t' - \tau|\right),$$

where $M=M_1+iM_2$ if $t \leq T_2$; and $M=M_{1-st}+iM_{2-st}$ if $t>T_2$.

Averaging for powder is performed in accordance with the following equation:

$$M_{echo-powder} = \frac{1}{2}\int_{-1}^{1} M_{echo} \cos\vartheta_p d(\cos\vartheta_p) \quad (34)$$

Figure 2:
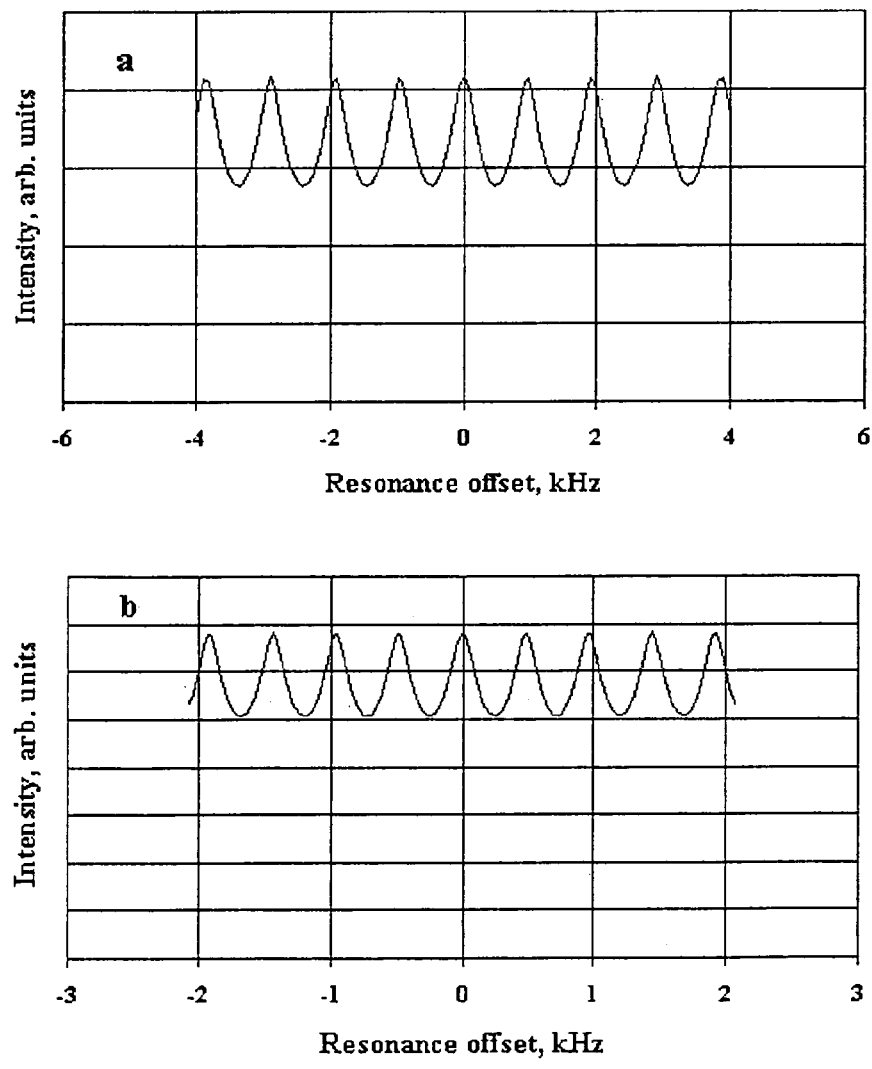
FIG. 2a is a graph showing the dependence of the calculated amplitude of the NQR signal plotted with respect to resonance offset in kHz, after a Fourier transform of the difference between the carrier frequency of the RF pulses of the SLSE sequence and the frequency of the resonance transition, if the sequence duration is $\sim T_2$.
FIG. 2b shows a similar graph of the same dependence, but the situation if the duration of the sequence is $\gg T_2$.

In FIG. 2a the dependence of the amplitude of the Fourier-transform $M_{echo-powder}$ on the difference between the carrier frequency of the RF pulses of the SLSE sequence and the resonance transition frequency when the duration of the sequence is ~$T_2$ is shown, and FIG. 2b shows the same dependence when the duration of the sequence is >>$T_2$.

The parameters chosen for the theoretical calculation in FIG. 2a are as follows: $\gamma H_1 t_w = 119°$, $t_{w0} = 80$ µs, $t_w = 80$ µs, $\tau = 1$ ms, $T_2 = 260$ ms, $T_2^* = 250$ µs, $n = 200$, which correspond to line $\nu_+ = 5301$ kHz of HMX at a temperature of 300° K. The parameters chosen for the theoretical calculation in FIG. 2b are as follows: $\gamma H_1 t_w = 119°$, $t_{w0} = 80$ µs, $t_w = 80$ µs, $\tau = 2$ ms, $T_2 = 3.3$ ms, $T_2^* = 2.6$ ms, $n = 200$. These parameters correspond to line $\nu_- = 3600$ kHz of $NaNO_2$ at a temperature of 300° K.

The comparison of the theoretical calculation with experimental results was done using two powder samples: HMX (line $\nu_+ = 5301$ kHz) and $NaNO_2$ (line $\nu_- = 3600$ kHz) at room temperature. The mass of the sample was 50 g for HMX and 40 g for $NaNO_2$. The volume of the detector coil was approximately 1 litre. The peak power of the transmitter was 280 W.

Figure 3:
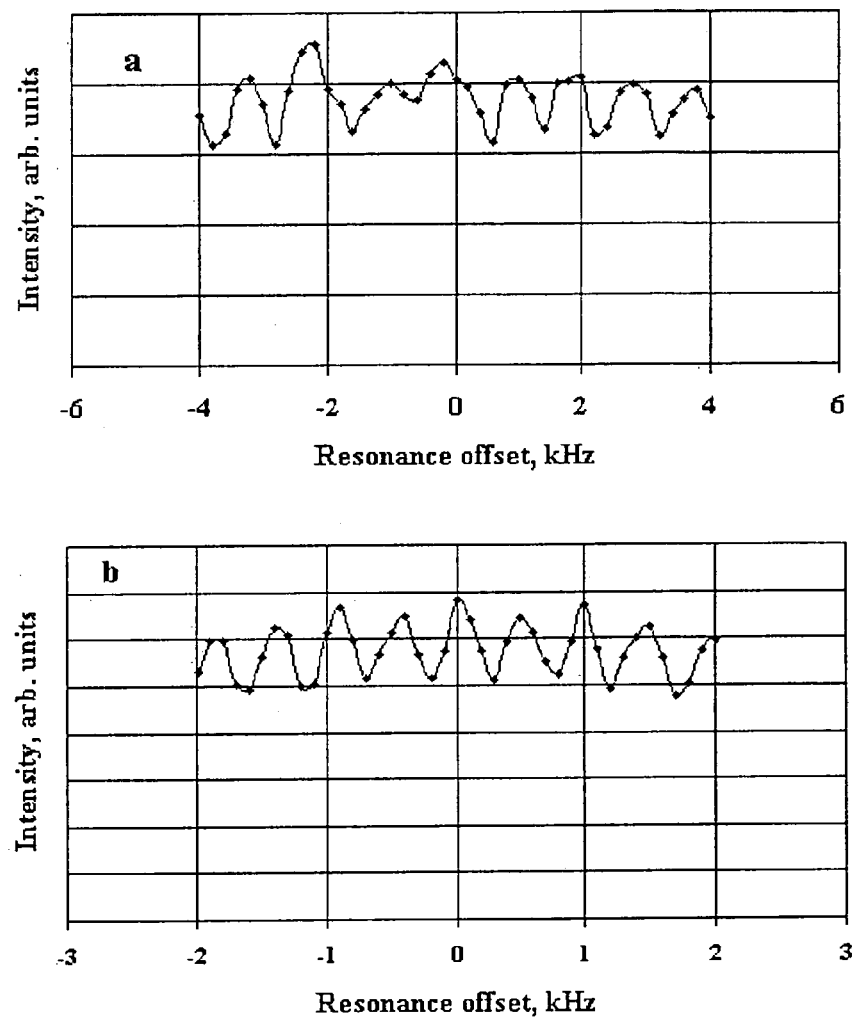

The parameters of the sequence SLSE $\phi_{0x}-(\tau-\phi_y-\tau)_n$ with which the sample was irradiated corresponded to those used for the calculation. The result of the dependence of the amplitude of the NQR echo signal on the frequency offset is presented in FIG. 3a for HMX and FIG. 3b for $NaNO_2$.

The theoretical and experimental results demonstrate it is possible to use the echo sequences to eliminate the intensity anomalies.

Now describing specific embodiments of the best mode for carrying out the invention, the best mode for carrying out the invention is concerned with using multi-pulse RF sequences to excite an NQR signal in a substance containing quadrupole nuclei with either integer or half-integer spins for the purposes of detecting such a signal.

The particular apparatus for producing pulse sequences of this kind comprises a pulse generator, the hardware design of which is known, and described in the applicant's corresponding International Patent Application PCT/AU00/01214 (WO 01/25809), which is incorporated herein by reference.

In order to generate a pulse sequence, firstly a pulse programmer is used to create a low voltage level pulse sequence. Such programmer is capable of generating a continuous sine wave of a desired frequency (eg; 0.89 or 5.2 MHz) and of any phase by using a Direct Digital Synthesizer (DDS) or any RF source. To create a pulse sequence, a gate is used to divide the continuous sine wave into small pulses. For example, the gate switches on for ~300 μs and off for ~300 μs, repeatedly thereby creating a sequence of pulses. The user of the pulse generator generates the pulse sequence via a computer program in the controlling computer. The computer program enables the user to input the frequency, phase, duration and separation of any pulses and allows the user to repeat any parts of the pulse sequence in a loop. The entire pulse sequence is contained in the program and then converted into binary and sent to the pulse programmer and stored in memory. The CPU of the pulse programmer then takes the machine code stored in memory and creates the pulse sequence by changing the frequency and phase of the DDS and providing instructions to the gate as to when to switch, thereby creating the pulses.

A simplified example of the program used to create a pulse sequence is outlined below:
Set Transmit Frequency: 0.89 MHz
Set Phase: 0 degrees
Gate Open
Wait 300 μs
Gate Closed (thus first pulse is created 300 μs long of phase 0 degrees)
Wait 300 μs
Set Transmit Frequency: 0.89 MHz
Set Phase: 90 degrees
For 1000 loops
  Gate Open
  Wait 300 μs
  Gate Closed
  Wait 300 μs
End of Loop (thus 1000 additional pulses are created each 300 μs long and spaced 300 μs of a phase 90 degrees).

Secondly, each pulse sequence is transmitted to the coil via a high power amplifier (1→5 kW), which amplifies the low voltage signal created by the pulse programmer to a higher voltage level which is sufficient to stimulate the nitrogen 14 nuclei.

Figure 4:
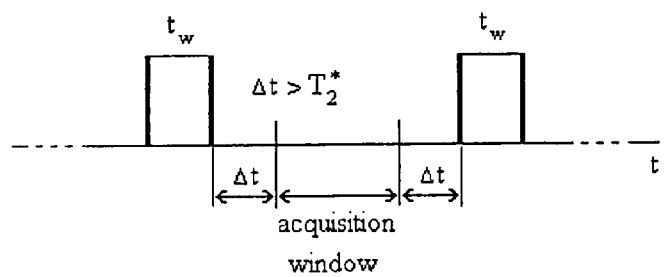
FIG. 4 is a timing diagram showing an example of determining the acquisition window for an echo pulse sequence.

The first embodiment of the invention is directed towards improving the cancelling of temperature effects by using an echo sequence without any additional measures for reducing the induction signals or echo signals appearing at the end of the window and which are not connected with the preparatory pulse. To separate the echo component from the preparatory pulse, the acquisition time is set at an interval of $\Delta t$ from the preceding pulse and at the same interval from the posterior pulse, as shown in FIG. 4.

The following echo sequences are examples of the use of the first preferred embodiment:

SLSE $(\phi_0)_{0°}-\tau-(\phi_{90°}-\tau)_n$,
MW-2$(\phi_0)_{0°}-\tau-(\phi_{0°}-2\tau-\phi_{180°}-2\tau)_n$,
WAHUHA-4
  $(\phi_0)_{0°}-\tau-(\phi_{180°}-\tau-\phi_{90°}-2\tau-\phi_{270°}-\tau-\phi_{0°}-2\tau)_n$,
  $\phi_{0(45°)}-\tau-(\phi_{0°}-2\tau-\phi_{90°}-2\tau-_{180°}-2\tau-\phi_{270°}-2\tau)_n$.

The difference between the above sequences and their steady-state analogs is that pulse separation in these sequences is at least several times longer than the $T_2^*$ time.

Figure 5A:
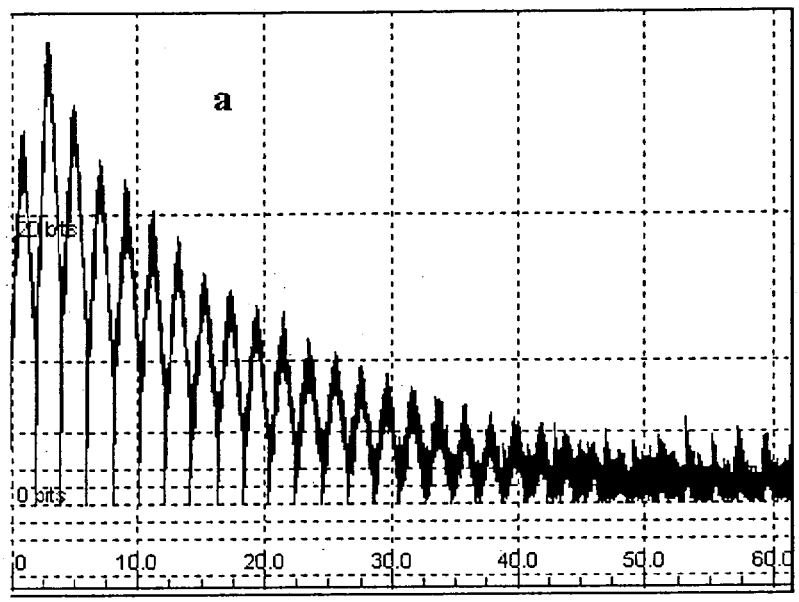
FIGS. 5a, 5b and 5c show echo signals received after using sequences $SLSE(\phi_0)_{0°}-\tau-(\phi_{90°}-2\tau[90°])_{n1}$, MW-2 $(\phi_0)_{0°}-\tau-(\phi_{0°}-2\tau-\phi_{180°}-2\tau[180°])_{n2}$ and WAHUHA-4$(\phi_0)_{0°}-\tau-(\phi_{180°}-\tau-\phi_{90°}-2\tau-\phi_{270°}-\tau-\phi_{0°}-2\tau[0°])_{n3}$, respectively, for $NaNO_2$ powder, wherein the acquisition time is set at the end of the sequence cycles at equal intervals from both the preceding and the posterior pulses for the purposes of isolating the echo part of the signal.
Figure 5B:
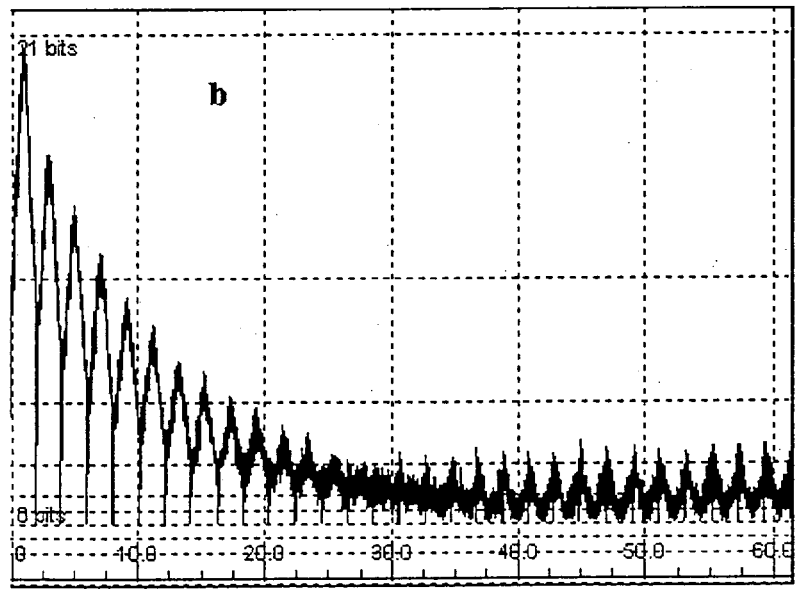
Figure 5C:
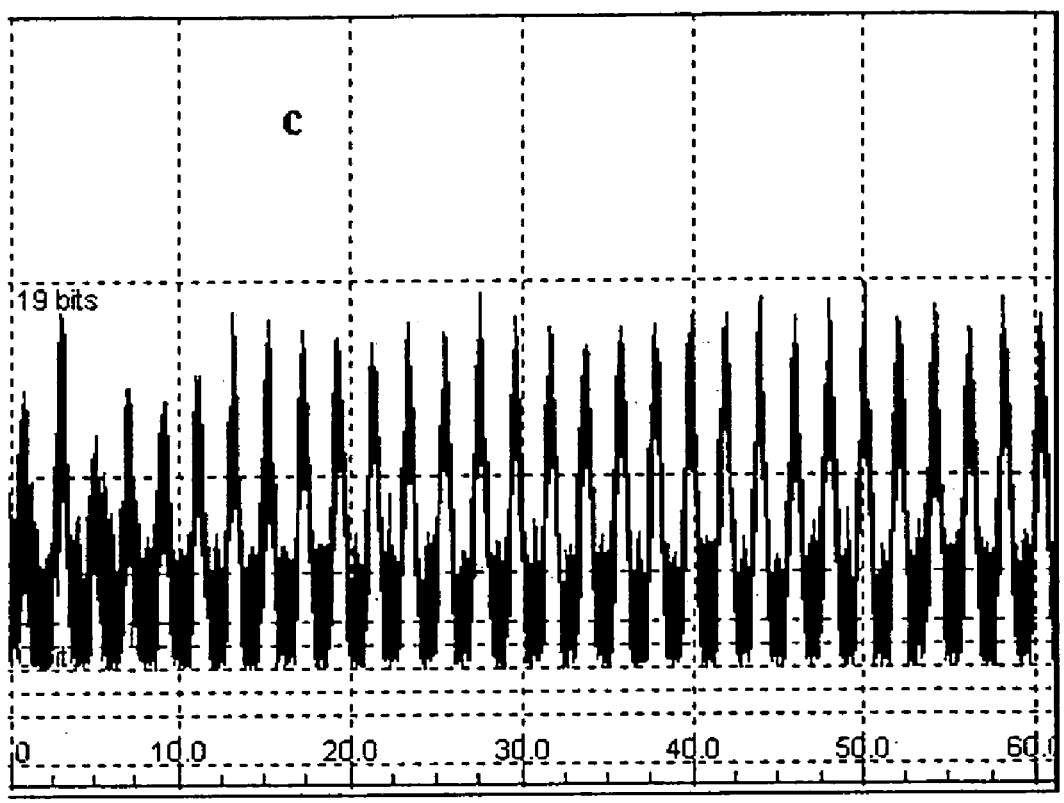

The types of echo signals that occur when using sequences SLSE $(\phi_0)_{0°}-\tau-(\phi_{90°}-2\tau[90°])_{n1}$, MW-2$(\phi_0)_{0°}-\tau-(\phi_{0°}-2\tau-_{180°}-2\tau[180°])_{n2}$ and WAHUHA-4$(\phi_0)_{0°}-\tau-(\phi_{180°}-\tau-\phi_{90°}-2\tau-\phi_{270°}-\tau-\phi_{0°}-2\tau[0°])_{n3}$ for NaNO$_2$ powder are presented in FIGS. 5a, 5b and 5c respectively (square brackets in the sequence formulas contain the receiver phase).

Sequence parameters are as follows: $\tau=1980$ μs, $t_{w0}=80$ μs, $t_w=172$ μs, $\phi_0=\gamma H_1 t_{w0} \approx 119°$, $\phi=\gamma H_1 t_w > 257°$, n=30.

The echo signal was measured only after the last pulse of the cycle. The length of the offset between the last pulse of the offset and acquisition time, and also between acquisition time and the first pulse of the following cycle (see FIG. 4) for all sequences was chosen to be the same $\Delta t=870$ μs. The duration of the acquisition time was also the same and equalled 3072 μs. All measurements were carried out at a temperature of 21° C.

The second embodiment of the invention is directed towards improving the diminishing effects of temperature by using a combination of sequences organised so as to cancel all signals, except for the echo signals generated by the preparatory pulse.

The third embodiment is directed towards a variant of the second embodiment, where the combination contains two sequences, the first sequence containing a preparatory pulse and the second sequence being different from the first by at least one parameter of the preparatory pulse, or the second sequence not having a preparatory pulse at all.

The receiver phases during the action of the second sequence follow the phases of the first sequence with an additional phase shift of 180°.

Examples of use of the third embodiment are:

$(\phi_0)_{0°}-\tau-(\phi_{90°}-2\tau[0°])_n$ and $(\phi_{90°}-2\tau[180°])_n$, $(\phi_0)_{0°}-\tau-(\phi_{90°}-2\tau[0°])_n$ and
  $(\phi_0)_{180°}-\tau-(\phi_{90°}-2\tau[180°])_n$.

Here the square brackets contain the phase of the receiver.

The fourth embodiment is directed towards a second variant of the second embodiment, where the combination consists of two sequences that differ by the phases of all pulses, except the preparatory ones, by 180°. The preparatory pulse in the second sequence can differ from the preparatory pulse of the first sequence by any number of parameters or can coincide with it completely. The receiver phases for both sequences are identical.

Some examples of the third embodiment are:

$(\phi_0)_{0°}-\tau-(\phi_{90°}-2\tau[0°])_n$ and $(\phi_{270°}-2\tau[0°])_n$, $(\phi_0)_{0°}-\tau-(\phi_{90°}-2\tau[0°])_n$ and $(\phi_0)_{0°}-\tau-(\phi_{270°}-2\tau[0°])_n$.

The third and the fourth embodiments are basically applicable to those sequences where the duration T lies within the limits $T_2 \ll T < T_{2e}$.

The fifth embodiment is directed towards a third variant of the second embodiment, where the combinations used consist of four sequences which are differentiated by the pulse phases as shown in the following Table.

TABLE 1

| | Phase of the preparatory pulse | Phase of the n-th pulse of the sequence | Receiver phase |
|---|---|---|---|
| 1st sequence | $\varphi_0$ | $\varphi_n$ | $\varphi_{receiver}$ |
| 2nd sequence | $\varphi_0$ | $\varphi_n + \pi$ | $\varphi_{receiver}$ |

TABLE 1-continued

| | Phase of the preparatory pulse | Phase of the n-th pulse of the sequence | Receiver phase |
|---|---|---|---|
| 3rd sequence | $\varphi_0$ | $\varphi_n + \dfrac{\pi}{2}$ | $\varphi_{reciever} + \pi$ |
| 4th sequence | $\varphi_0$ | $\varphi_n - \dfrac{\pi}{2}$ | $\varphi_{reciever} + \pi$ |

The fifth embodiment is intended mainly for sequences which have a duration T comparable with the relaxation time $T_2$.

An example of the fifth embodiment of the SLSE sequences is:

$(\phi_0)_{0°}-\tau-(\phi_{90°}-2\tau[0°])_n$, $(\phi_0)_{0°}-\tau-(\phi_{270°}-2\tau[0°])_n$, $(\phi_0)_{0°}-\tau-(\phi_{180°}-2\tau[180°])_n$ and
$(\phi_0)_{0°}-\tau-(\phi_{0°}-2\tau[180°])_n$.

It is preferable to set the time interval between the sequences ~$T_1$.

It should be appreciated that the scope of the present invention is not limited by the specific embodiments described herein.

The invention claimed is:

1. A nuclear quadrupole resonance apparatus for detecting a target substance containing quadrupole nuclei, comprising:
a pulse sequence generator to generate a combination of multi-pulse sequences with pulse intervals longer than the time constant of free induction decay $T_2^*$, but shorter than the time of spin-spin relaxation $T_2$, and to generate a preparatory pulse or group of preparatory pulses for creating echo signals between the pulses of the multi-pulse sequences;
a detector to detect nuclear quadrupole resonance signals generated from the target substance under conditions of unknown temperature of the target substance in response to the combination of multi-pulse sequences; and
a combiner to combine the detected nuclear quadrupole resonance signals generated under conditions of unknown temperature of the target substance into a resulting signal such that the resulting signal contains a prevailing echo component produced by the preparatory pulse or group of preparatory pulses, thereby mitigating the effect of intensity variations.

2. A method of nuclear quadrupole resonance for detecting a target substance containing quadrupole nuclei, the method comprising the steps of:
generating a combination of multi-pulse sequences, at least one of which contains a preparatory pulse or group of preparatory pulses, having intervals between pulses longer than the time constant of free induction decay $T_2^*$, but shorter than the time of spin-spin relaxation $T_2$;
irradiating the target substance with the combination of multi-pulse sequences;
detecting nuclear quadrupole resonance signals generated from the target substance under conditions of unknown temperature of the target substance in response to the combination of multi-pulse sequences; and
combining the detected nuclear quadrupole resonance signals generated under conditions of unknown temperature of the target substance into a resulting signal where echo generated by the preparatory pulse or group of preparatory pulses is a prevailing components, thereby mitigating the effect of intensity variations.

3. A method as claimed in claim 2, wherein the combination contains at least one sequence.

4. A method as claimed in claim 2, wherein the flip angles of pulses of sequences of the combination range between 60° and 345°.

5. A method as claimed in claim 2, wherein at least one preparatory pulse is composite.

6. A method as claimed in claim 2, wherein all pulse sequences of the combination contain a preparatory pulse or a group of preparatory pulses.

7. A method as claimed in claim 2, wherein the carrier frequency of the pulse sequences is near to one of NQR frequencies of the target substance to be detected.

8. A method as claimed in claim 2, wherein the target substance to be detected comprises an explosive containing quadrupole nuclei.

9. A method as claimed in claim 2, wherein the target substance to be detected comprises a narcotic containing quadrupole nuclei.

10. An apparatus for producing a multi-pulse sequence for irradiating a target substance containing quadrupole nuclei, comprising:
a generator to generate a combination of multi-pulse sequences with pulse intervals longer than the time constant of free induction decay $T_2^*$, but shorter than the time of spin-spin relaxation $T_2$, and containing a preparatory pulse or group of preparatory pulses for creating echo signals between the pulses of the multi-pulse sequences organised so that the resulting signal contains a prevailing echo component produced by the preparatory pulse or group of preparatory pulses; and
a detector to detect nuclear quadrupole resonance signals generated from the target substance under conditions of unknown temperature of the target substance in response to the combination of multi-pulse sequences.

11. A nuclear quadrupole resonance apparatus for detecting a target substance containing quadrupole nuclei, comprising:
means for generating a combination of multi-pulse sequences with pulse intervals longer than the time constant of free induction decay $T_2^*$, but shorter than the time of spin-spin relaxation $T_2$, and for generating a preparatory pulse or group of preparatory pulses for creating echo signals between the pulses of the multi-pulse sequences;
means for detecting nuclear quadrupole resonance signals generated from the target substance under conditions of unknown temperature of the target substance in response to the combination of multi-pulse sequences; and
means for combining the detected nuclear quadrupole resonance signals into a resulting signal such that the resulting signal contains a prevailing echo component produced by the preparatory pulse or group of preparatory pulses, thereby mitigating the effect of intensity variations.

12. An apparatus for producing a multi-pulse sequence for irradiating a target substance provided with quadrupole nuclei, comprising:
generator means for generating a combination of multi-pulse sequences with pulse intervals longer than the time constant of free induction decay $T_2^*$, but shorter than the time of spin-spin relaxation $T_2$, and containing a preparatory pulse or group of preparatory pulses for creating echo signals between the pulses of the multi-pulse sequences organised so that the resulting signal contains a prevailing echo component produced by the preparatory pulse or group of preparatory pulses; and detector means for detecting nuclear quadrupole resonance signals generated from the target substance under conditions of unknown temperature of the target substance in response to the combination of multi-pulse sequences.

* * * * *